US011865064B2

(12) United States Patent
Ovalle (10) Patent No.: US 11,865,064 B2
(45) Date of Patent: *Jan. 9, 2024

(54) REMOTE SPA CONTROL SYSTEM

(71) Applicant: Sundance Spas, Inc., Chino, CA (US)

(72) Inventor: Larry R. Ovalle, Chino, CA (US)

(73) Assignee: Sundance Spas, Inc., Chino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/805,084

(22) Filed: Jun. 2, 2022

(65) Prior Publication Data

US 2022/0347050 A1 Nov. 3, 2022

Related U.S. Application Data

(63) Continuation of application No. 17/303,172, filed on May 21, 2021, now Pat. No. 11,376,190, which is a
(Continued)

(51) Int. Cl.
*A61H 33/00* (2006.01)
*H04Q 9/00* (2006.01)
(Continued)

(52) U.S. Cl.
CPC ....... *A61H 33/005* (2013.01); *A61H 33/0095* (2013.01); *H04Q 9/00* (2013.01); *A61H 2033/0054* (2013.01); *A61H 2033/0079* (2013.01); *A61H 2201/0207* (2013.01); *A61H 2201/1207* (2013.01);
(Continued)

(58) Field of Classification Search
CPC .... A61H 33/005; A61H 33/0095; H04Q 9/00; H04W 4/12
See application file for complete search history.

(56) References Cited

U.S. PATENT DOCUMENTS 7,167,087 B2   1/2007   Corrington et al.
7,292,898 B2   11/2007  Clark et al.
(Continued)

FOREIGN PATENT DOCUMENTS

EP   3094223   3/2019
EP   3225765   9/2020
(Continued)

*Primary Examiner* — Jeremy Carroll
(74) *Attorney, Agent, or Firm* — Knobbe, Martens, Olson & Bear, LLP (57) ABSTRACT

A spa is provided including a frame, a shell mounted to the frame defining a basin for holding water, at least one sensor for monitoring a spa component or water condition, a communications interface including a cellular transceiver, and a battery for providing power to the at least one sensor and to the communications interface when the spa is not connected to a power source. The spa also includes a controller in electrical communication with the at least one sensor and the communications interface. The controller is configured to, while the spa is not connected to the power source, receive information from the at least one sensor, process the received information, and cause the communications interface to wirelessly transmit the processed information to a remote source or central server.

22 Claims, 7 Drawing Sheets

Related U.S. Application Data continuation of application No. 17/181,520, filed on Feb. 22, 2021, which is a continuation of application No. 16/148,384, filed on Oct. 1, 2018, now Pat. No. 10,925,804.

(60) Provisional application No. 62/567,908, filed on Oct. 4, 2017.

(51) Int. Cl.
  *H04W 84/12* (2009.01)
  *G01S 19/03* (2010.01)
  *G01N 33/18* (2006.01)
  *G01S 19/13* (2010.01)

(52) U.S. Cl.
  CPC .............. *A61H 2201/5012* (2013.01); *A61H 2201/5046* (2013.01); *A61H 2201/5058* (2013.01); *A61H 2201/5064* (2013.01); *A61H 2201/5082* (2013.01); *A61H 2201/5084* (2013.01); *A61H 2201/5087* (2013.01); *A61H 2201/5092* (2013.01); *A61H 2201/5097* (2013.01); *G01N 33/18* (2013.01); *G01S 19/13* (2013.01); *H04Q 2209/30* (2013.01); *H04Q 2209/43* (2013.01); *H04Q 2209/86* (2013.01); *H04Q 2209/88* (2013.01); *H04W 84/12* (2013.01)

(56) References Cited

U.S. PATENT DOCUMENTS

| | | |
|---|---|---|
| 7,397,360 B2 | 7/2008 | Corrington et al. |
| 7,489,986 B1 | 2/2009 | Laflamme et al. |
| 7,982,625 B2 | 7/2011 | Brochu et al. |
| 8,112,164 B2 | 2/2012 | Hollaway |
| 8,164,470 B2 | 4/2012 | Brochu et al. |
| 8,301,270 B2 | 10/2012 | Quail |
| 8,307,484 B2 | 11/2012 | Porat |
| 8,467,908 B2 | 6/2013 | Broniak et al. |
| 8,612,061 B2 | 12/2013 | Laflamme et al. |
| 8,624,749 B2 | 1/2014 | Brochu et al. |
| 8,644,960 B2 | 2/2014 | Laflamme et al. |
| 8,649,908 B2 | 2/2014 | Nibler et al. |
| 8,688,280 B2 | 4/2014 | Macey |
| 8,795,510 B2 | 8/2014 | Porat |
| 8,831,584 B2 | 9/2014 | Almeda |
| 8,838,280 B2 | 9/2014 | Macey |
| 8,914,310 B2 | 12/2014 | Moroney et al. |
| 9,058,027 B2 | 6/2015 | Macey |
| 9,084,314 B2 | 7/2015 | Conover et al. |
| 9,097,234 B2 | 8/2015 | Breau et al. |
| 9,100,999 B2 | 8/2015 | Li |
| 9,158,292 B2 | 10/2015 | Quail |
| 9,250,626 B2 | 2/2016 | Michelon |
| 9,326,912 B2 | 5/2016 | Nicholson |
| 9,405,441 B2 | 8/2016 | Trafton et al. |
| 9,414,142 B1 | 8/2016 | Zauhar et al. |
| 9,442,639 B2 | 9/2016 | Laflamme et al. |
| 9,631,388 B2 | 4/2017 | Hui et al. |
| 9,633,547 B2 | 4/2017 | Farrand et al. |
| 9,655,810 B2 | 5/2017 | Macey |
| 9,663,547 B2 | 5/2017 | Lansalot-matras et al. |
| 9,740,199 B2 | 8/2017 | Michelon |
| 9,787,072 B2 | 10/2017 | Potucek et al. |
| 9,807,855 B2 | 10/2017 | Lyons et al. |
| 9,808,397 B2 | 11/2017 | Breau et al. |
| 9,810,599 B2 | 11/2017 | Bright |
| 9,901,511 B2 | 2/2018 | Kang et al. |
| 10,037,675 B2 | 7/2018 | Uy |
| 10,062,259 B2 | 8/2018 | Sentosa et al. |
| 10,127,362 B2 | 11/2018 | Bennett et al. |
| 10,167,649 B2 | 1/2019 | Khamis et al. |
| 10,198,929 B2 | 2/2019 | Snyder |
| 10,224,623 B1 | 3/2019 | Spears |
| 10,375,543 B2 | 8/2019 | Mcqueen et al. |
| 10,396,592 B2 | 8/2019 | Forbes, Jr. |
| 10,492,268 B2 | 11/2019 | Potucek |
| 10,537,034 B2 | 1/2020 | Uy et al. |
| 10,610,448 B2 | 4/2020 | Chang et al. |
| 10,613,130 B1 | 4/2020 | Forood et al. |
| 10,616,955 B1 | 4/2020 | Zack |
| 10,618,136 B2 | 4/2020 | Bauckman et al. |
| 10,665,073 B1 | 5/2020 | Richerson, Jr. |
| 10,681,793 B1 | 6/2020 | Sanson |
| 10,683,675 B2 | 6/2020 | Walsh et al. |
| 10,731,369 B2 | 8/2020 | Khamis et al. |
| 10,801,225 B1 | 10/2020 | Reddy et al. |
| 10,831,083 B1 | 11/2020 | Rejniak et al. |
| 10,878,684 B1 | 12/2020 | Eller |
| 10,904,986 B1 | 1/2021 | Reddy et al. |
| 10,909,834 B2 | 2/2021 | Uy |
| 10,925,804 B2 | 2/2021 | Ovalle |
| 10,931,472 B2 | 2/2021 | Khalid et al. |
| 10,942,493 B2 | 3/2021 | Ball |
| 10,942,989 B2 | 3/2021 | Bennett et al. |
| 10,942,990 B2 | 3/2021 | Bennett et al. |
| 10,972,305 B2 | 4/2021 | Guilfoyle et al. |
| 10,976,713 B2 | 4/2021 | Potucek et al. |
| 10,985,939 B2 | 4/2021 | Clark et al. |
| 11,000,449 B2 | 5/2021 | Potucek et al. |
| 11,040,892 B2 | 6/2021 | Decket et al. |
| 11,112,799 B2 | 9/2021 | Simik et al. |
| 11,232,695 B1 | 1/2022 | Hausler |
| 11,270,567 B2 | 3/2022 | Tomas et al. |
| 11,319,722 B2 | 5/2022 | Jensen et al. |
| 11,320,102 B2 | 5/2022 | Tsao et al. |
| 11,376,190 B2 * | 7/2022 | Ovalle .............. A61H 33/005 |
| 2002/0035403 A1 | 3/2002 | Clark et al. |
| 2006/0238931 A1 | 10/2006 | Cline |
| 2007/0093920 A1 * | 4/2007 | Tarpo .............. A61H 33/60 |
|  |  | 700/65 |
| 2009/0255049 A1 | 10/2009 | Rosenau |
| 2010/0070059 A1 * | 3/2010 | Laflamme .............. G06F 3/162 |
|  |  | 704/275 |
| 2011/0031323 A1 | 2/2011 | Nold et al. |
| 2012/0252488 A1 * | 10/2012 | Hartmann .............. G06Q 10/08 |
|  |  | 455/456.1 |
| 2012/0271671 A1 | 10/2012 | Zaloom |
| 2014/0303781 A1 * | 10/2014 | Potucek .............. G05B 15/02 |
|  |  | 700/275 |
| 2015/0238384 A1 * | 8/2015 | Macey .............. H04L 67/125 |
|  |  | 700/282 |
| 2015/0302733 A1 * | 10/2015 | Witkowski .............. G07C 5/0808 |
|  |  | 340/5.25 |
| 2015/0362925 A1 | 12/2015 | Uy et al. |
| 2016/0342323 A1 | 11/2016 | Laflamme et al. |
| 2017/0071821 A1 | 3/2017 | Laflamme et al. |
| 2017/0211285 A1 * | 7/2017 | Potucek .............. E04H 4/16 |
| 2017/0275905 A1 | 9/2017 | Liu |
| 2018/0240322 A1 | 8/2018 | Potucek et al. |
| 2018/0270548 A1 * | 9/2018 | Richter .............. H04Q 9/00 |
| 2019/0314243 A1 | 10/2019 | MacCallum et al. |
| 2020/0137534 A1 | 4/2020 | Mcqueen et al. |
| 2020/0150633 A1 | 5/2020 | Goldman et al. |
| 2020/0221653 A1 | 7/2020 | Heaton |
| 2020/0271635 A1 | 8/2020 | Key et al. |
| 2021/0010989 A1 | 1/2021 | Yizhack et al. |
| 2021/0051787 A1 | 2/2021 | Sanson |
| 2021/0072729 A1 | 3/2021 | Niu |
| 2021/0108643 A1 | 4/2021 | Stiles et al. |
| 2021/0244612 A1 | 8/2021 | Ovalle |
| 2021/0317007 A1 | 10/2021 | Decker et al. |
| 2021/0327246 A1 | 10/2021 | Shlomovitz et al. |
| 2021/0366259 A1 | 11/2021 | Guzelgunler |
| 2021/0382485 A1 | 12/2021 | Simik et al. |
| 2021/0386620 A1 | 12/2021 | Zack et al. |
| 2022/0042335 A1 | 2/2022 | Besnier et al. |
| 2022/0251861 A1 | 8/2022 | Vaughn et al. |

(56) References Cited

U.S. PATENT DOCUMENTS

2022/0251862 A1  8/2022  Jensen et al.
2022/0252476 A1  8/2022  Steinbauer et al.

FOREIGN PATENT DOCUMENTS

| EP | 3702776 | 9/2020 |
|---|---|---|
| EP | 3840235 | 6/2021 |
| EP | 3914854 | 12/2021 |
| EP | 4008857 | 6/2022 |
| EP | 4039917 | 8/2022 |
| WO | WO 2007040490 | 4/2007 |
| WO | WO 2013110577 | 8/2013 |
| WO | WO 2014071278 | 5/2014 |
| WO | WO 2014164939 | 10/2014 |
| WO | WO 2016145253 | 9/2016 |
| WO | WO 2019070836 | 4/2019 |
| WO | WO 2019089340 | 5/2019 |
| WO | WO 2019152665 | 8/2019 |
| WO | WO 2020102115 | 5/2020 |
| WO | WO 2020159435 | 8/2020 |
| WO | WO 2021214656 | 10/2021 |
| WO | WO 2022011413 | 1/2022 |
| WO | WO 2022029713 | 2/2022 |
| WO | WO 2022157260 | 7/2022 |

* cited by examiner

REMOTE SPA CONTROL SYSTEM

CROSS-REFERENCE TO RELATED APPLICATIONS

This application claims priority to U.S. Provisional Patent Application No. 62/567,908, filed Oct. 4, 2017, which is hereby incorporated by reference in its entirety.

BACKGROUND OF THE INVENTION

Field of the Invention

The invention relates generally to a spa or hot tub including a communications interface for wired or wireless communication with remote computer networks and, in particular, a remote spa control and monitoring system accessible through a web portal or website.

Description of Related Art

Spas include variable features or functions, which are available to enhance a user's experience in the spa. For example, spas also often include sensors and electronic circuitry for monitoring spa conditions (e.g., water temperature, turbidity, chemical concentrations). Output from such sensors can be used to monitor spa operation and to emit an alert or notification if a fault is detected. Other spa features can include self-testing and alert generating components, water pumps, water jets, lights, and stereo systems. Typically, these features or functions have been controlled by a main control panel, such as a touchscreen built into the spa tub. Sensor readings may also be displayed on the main control panel. In some spa systems, functions can also be controlled by a dedicated remote control device, which can transmit commands to the spa.

In addition, a number of systems are known for transmitting sensor output from a spa to a remote computer network or device. Transmitted information can be accessed through a website or App to provide users with real time or periodically updated information about the spa.

For example, U.S. Pat. Nos. 7,982,625, 8,164,470, and 8,624,749 to Brochu et al. are directed to methods of monitoring a bathing system which measure electrical current drawn by the bathing system to determine whether the system is operating under normal or abnormal operating conditions. Results of the comparison can be transmitted wirelessly to a remote device.

U.S. Pat. Nos. 8,644,960 and 9,442,639 to Laflamme et al. are directed to user interface displays which display information about different settings or operating modes, such as ambience settings or low energy modes, for a bathing system. The user interface can be accessed through a remote device, such as a smart phone. The user interface can provide information about how long an ambience setting or mode has been in use, or about what operational settings of the bathing unit are associated with a selected ambience setting.

However, improved spa communication and control systems would be of benefit. For example, systems which improve accessibility of sensor information and which provide more robust remote control of the spa would improve user experiences. The devices and systems disclosed herein are designed to provide such benefits.

SUMMARY OF THE INVENTION

According to an aspect of the disclosure, a spa includes a frame, a shell mounted to the frame defining a basin for holding water, at least one sensor for monitoring a spa component or water condition, a communications interface comprising a cellular transceiver, a battery for providing power to the at least one sensor and to the communications interface when the spa is not connected to a power source, and a controller. The controller is in electrical communication with the at least one sensor and the communications interface. The controller is configured to, while the spa is not connected to the power source, receive information from the at least one sensor, process the received information, and cause the communications interface to wirelessly transmit at least a portion of the processed information to a remote source or central server.

According to another aspect of the disclosure, a system for performing remote diagnostics for a spa includes at least one spa and a central server. The spa includes a power and/or current sensor for measuring power use and/or current drawn by one or more spa components and a communications interface for wirelessly transmitting information measured by the at least one power and/or current sensor to a remote network or device. The central server, which is remote from the spa, includes computer readable memory including baseline measurements for the at least one spa obtained prior to initial installation of the spa. The central server is configured to: receive information collected by the at least one power and/or current sensor of the spa from the communications interface of the at least one spa; process the received information to determine power and/or current measurements for the one or more spa components; compare the power and/or current measurements to the baseline measurements stored on the computer readable memory of the central server; and identify one or more faults for the spa components of the at least one spa based on the comparison.

According to another aspect of the disclosure, a remote control and monitoring system for a spa includes at least one spa, a web-enabled portable computer device, and a central server. The at least one spa includes at least one sensor for monitoring water condition or status of a spa component and a communications interface including a cellular transceiver for wirelessly transmitting information obtained from the at least one sensor to a remote device over a cellular network. The central server in wireless communication with the at least one spa and with the portable computer device. The central server is configured to: receive information from the at least one sensor of the at least one spa over the cellular network; process the received information to determine one or more water condition parameters for water contained in the spa; generate a web portal displaying the one or more water condition parameters; and transmit the web portal to the web-enabled portable computer device over the Internet, so that the one or more water condition parameters can be viewed by a user.

According to another aspect of the disclosure, a method for performing remote diagnostics for at least one spa includes receiving on a computer server remote from the at least one spa information collected by at least one power and/or current sensor of the at least one spa. The information is transmitted from the spa to the computer server via a communications interface of the at least one spa. The method also includes processing the received information to determine power and/or current measurements for one or more spa components of the at least one spa and comparing the power and/or current measurements for the one or more spa components to baseline measurements for the one or more spa components of the at least one spa. The baseline measurements can be obtained prior to initial installation of the spa. The method also includes identifying one or more faults for the one or more spa components of the at least one spa based on the comparison.

Further preferred and non-limiting embodiments or aspects of the present invention will now be described in the following numbered clauses:

Clause 1: A spa comprising: a frame; a shell mounted to the frame defining a basin for holding water; at least one sensor for monitoring a spa component or water condition; a communications interface comprising a cellular transceiver; a battery for providing power to the at least one sensor and to the communications interface when the spa is not connected to a power source; and a controller in electrical communication with the at least one sensor and the communications interface configured to, while the spa is not connected to the power source, receive information from the at least one sensor, process the received information, and cause the communications interface to wirelessly transmit at least a portion of the processed information to a remote source or central server.

Clause 2: The spa of clause 1, wherein the at least one sensor for monitoring water condition comprises one or more of a water temperature sensor, a water care sensor for measuring water pH or sanitizer levels of spa water, a turbidity sensor, an optical sensor for reading an image of an analyte test strip, an ambient temperature sensor, an ambient humidity sensor, and a water level sensor.

Clause 3: The spa of clause 1, wherein the at least one sensor comprises one or more of the following sensors for measuring a condition of spa components: a flow sensor for measuring water flow through a spa filter, a power sensor, an electrical current sensor, a battery level sensor, and location determining circuitry.

Clause 4: The spa of any of clauses 1 to 3, further comprising a WiFi adapter in wired or wireless communication with the controller via the cellular transceiver, the WiFi adapter being configured to receive information from the cellular transceiver and to wirelessly retransmit the received information to a remote computer network via WiFi.

Clause 5: The spa of any of clauses 1 to 4, wherein the controller is configured to receive instructions for operating the spa from a remote computer network via the communications interface and to adjust an operating parameter of one or more spa components based on the received instructions.

Clause 6: The spa of any of clauses 1 to 5, wherein the controller is configured to generate one or more errors or notifications based, at least in part, on information received from the at least one sensor, and wherein the controller is configured to transmit the errors or notifications to a remote computer network via the cellular transceiver.

Clause 7: The spa of clause 1, wherein the at least one sensor comprises at least one water level sensor, and wherein the controller is configured to: determine a water level of the spa based on information received from the at least one water level sensor, and transmit information representative of the water level of the spa to a remote computer network via the cellular transceiver.

Clause 8: The spa of clause 7, wherein the information representative of the water level of the spa comprises a notification that the spa is nearly full or a notification that the spa is empty.

Clause 9: The spa of clause 1, wherein the at least one sensor comprises: at least one accelerometer mounted to the frame or basin of the spa for detecting if the spa is dropped during shipping; and location determining circuitry connected to the spa for monitoring a location of the spa during shipping.

Clause 10: The spa of clause 9, wherein the location determining circuitry comprises a global positioning system (GPS) device.

Clause 11: The spa of clause 9 or clause 10, wherein the controller is configured to periodically transmit location information for the spa determined by the location determining circuitry to a remote computer network via the cellular transmitter.

Clause 12: The system of any of clauses 9-11, wherein the controller is configured to: receive movement information for the spa from the accelerometer; process the received information to detect if the spa has been dropped; and if it is determined that the spa has been dropped, cause the cellular transceiver to wirelessly transmit a notification to a remote computer network comprising information about a condition of the spa via the cellular transceiver.

Clause 13: The system of clause 12, wherein the notification comprising an indication that the spa has been dropped and information about a location of the spa determined from the location determining circuitry.

Clause 14: A system for performing remote diagnostics for a spa comprising: at least one spa comprising a power and/or current sensor for measuring power use and/or current drawn by one or more spa components and a communications interface for wirelessly transmitting information measured by the at least one sensor to a remote network or device; and a central server remote from the spa comprising computer readable memory including baseline measurements for the at least one spa obtained prior to initial installation of the spa, wherein the central server is configured to: receive information collected by the at least one power and/or current sensor of the spa from the communications interface of the at least one spa; process the received information to determine power and/or current measurements for the one or more spa components; compare the power and/or current measurements to the baseline measurements stored on the computer readable memory of the central server; and identify one or more faults for the spa components of the at least one spa based on the comparison.

Clause 15: The system of clause 14, wherein the communications interface of the spa comprises a cellular transceiver, and wherein the spa further comprises a battery for providing power to the communications interface when the spa is not connected to a power source Clause 16: The system of clause 14 or clause 15, wherein the spa is configured to periodically initiate a self-test, the self-test comprising cycling power to the one or more spa components and measuring power use and/or current drawn by the one or more components with the power and/or current sensor as the power cycles to the one or more spa components.

Clause 17: The system of clause 16, wherein the spa is configured to transmit information measured by the power and/or current sensor during the self-test to the central server according to a predetermined schedule following completion of the self-test.

Clause 18: The system of any of clauses 14-17, wherein the spa is configured to measure power use and/or current drawn by the one or more components with the power and/or current sensor in real time during normal operation of the spa.

Clause 19: The system of clause 18, wherein the spa is configured to transmit information measured by the power and/or current sensor to the central server in real time.

Clause 20: The system of any of clauses 14-19, wherein the central server is further configured to process the one or more faults to diagnose problems with the spa and/or spa components.

Clause 21: The system of clause 20, wherein the central server is further configured to generate an alert that one or more of the spa components is not functioning in an expected manner based on the processing of the one or more faults.

Clause 22: The system of clause 21, wherein the central server comprises a network interface, and wherein the central server is configured to transmit the alert to a remote electronic device via the network interface.

Clause 23: The system of any of clauses 14-22, wherein the central server is configured to wirelessly transmit one or more software updates to the spa in response to the identified faults.

Clause 24: A remote control and monitoring system for a spa comprising: at least one spa comprising at least one sensor for monitoring water condition or status of a spa component and a communications interface comprising a cellular transceiver for wirelessly transmitting information obtained from the at least one sensor to a remote device over a cellular network; a web-enabled portable computer device; and a central server in wireless communication with the at least one spa and the portable computer device, wherein the central server is configured to: receive information from the at least one sensor of the at least one spa over the cellular network; process the received information to determine one or more water condition parameters for water contained in the spa; generate a web portal displaying the one or more water condition parameters; and transmit the web portal to the web-enabled portable computer device over the Internet so that the one or more water condition parameters can be viewed by a user.

Clause 25: The remote control and monitoring system of clause 24, wherein the at least one sensor for monitoring water condition comprises one or more of a water temperature sensor, a water care sensor for measuring water pH or sanitizer levels of spa water, a turbidity sensor, an optical sensor for reading an image of an analyte test strip, an ambient temperature sensor, an ambient humidity sensor, and a water level sensor.

Clause 26: The remote control and monitoring system of clause 24, wherein the at least one sensor comprises one or more of the following sensors for measuring a condition of spa components: a flow sensor for measuring water flow through a spa filter, a power sensor, an electrical current sensor, a battery level sensor, and location determining circuitry.

Clause 27: The remote control and monitoring system of any of clauses 24-26, wherein the web portal comprises a water quality indicator comprising a visual icon representative of whether spa water is clear or cloudy determined based on the one or more water condition parameters.

Clause 28: The remote control and monitoring system of any of clauses 24-27, wherein the web portal further comprises dosing recommendations for applying spa chemicals to the spa water determined based on the one or more water condition parameters.

Clause 29: The remote control and monitoring system of any of clauses 24-28, wherein the web portal further comprises a maintenance alert section comprising a list of maintenance activities to be performed for the at least one spa determined, at least in part, based on the one or more water condition parameters.

Clause 30: The remote control and monitoring system of clause 29, wherein the list of maintenance activities of the web portal is determined based, at least in part, on the one or more water condition parameters.

Clause 31: The remote control and monitoring system of any of clauses 24-30, wherein the web portal further comprises a content section comprising instructional informal for operating the spa, and wherein the controller is configured to select instructional information to display in the content section based, at least in part, on an amount of time since initial spa installation and the one or more water condition parameters.

Clause 32: The remote control and monitoring system of any of clauses 24-31, wherein the web portal further comprises an energy cost estimator displaying an estimated operating cost range for the spa determined based, at least in part, a local energy rate input by a user.

Clause 33: The remote control and monitoring system of any of clauses 24-32, comprising a plurality of spas, wherein the web portal comprises a web portal for a spa dealer displaying information for each of the plurality of spas.

Clause 34: The remote control and monitoring system of clause 33, wherein the web portal for the spa dealer comprises a list of the plurality of spas, and wherein, in response to a user selection, status information for a selected spa of the plurality of spas is displayed on the web portal.

Clause 35: The remote control and monitoring system of any of clauses 24-32, comprising a plurality of spas, wherein the web portal displays information for a subgroup of the plurality of spas to a user determined based on an authorization level of the user.

Clause 36: A method for performing remote diagnostics for at least one spa, comprising: receiving on a computer server remote from the at least one spa information collected by at least one power and/or current sensor of the at least one spa, wherein the information is transmitted from the spa to the computer server via a communications interface of the at least one spa; processing the received information to determine power and/or current measurements for one or more spa components of the at least one spa; comparing the power and/or current measurements for the one or more spa components to baseline measurements for the one or more spa components of the at least one spa, wherein the baseline measurements are obtained prior to initial installation of the spa; and identifying one or more faults for the one or more spa components of the at least one spa based on the comparison.

Clause 37: The method of clause 36, further comprising processing the one or more faults to diagnose problems with the at least at least one spa, and generating an alert that one or more of the spa components is not functioning in an expected manner based on the processing of the one or more faults.

Clause 38: The method of clause 36 or clause 37, further comprising wirelessly transmitting one or more software updates from the computer server to the at least one spa via the communications interface of the at least one spa in response to the identified faults.

BRIEF DESCRIPTION OF THE DRAWINGS

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limit of the invention.

DETAILED DESCRIPTION

As used herein, the singular form of "a", "an", and "the" include plural referents unless the context clearly dictates otherwise. For the purposes of this specification, unless otherwise indicated, all numbers expressing quantities of ingredients, reaction conditions, dimensions, physical characteristics, and so forth used in the specification and claims are to be understood as being modified in all instances by the term "about."

As used herein, the terms "right", "left", "top", and derivatives thereof shall relate to the invention as it is oriented in the drawing figures. However, it is to be understood that the invention can assume various alternative orientations and, accordingly, such terms are not to be considered as limiting. Also, it is to be understood that the invention can assume various alternative variations and stage sequences, except where expressly specified to the contrary. It is also to be understood that the specific devices and processes illustrated in the attached drawings, and described in the following specification, are examples. Hence, specific dimensions and other physical characteristics related to the embodiments disclosed herein are not to be considered as limiting.

As used herein, the terms "communication" and "communicate" refer to the receipt or transfer of one or more signals, messages, commands, or other type of data. For one unit or component to be in communication with another unit or component means that the one unit or component is able to directly or indirectly receive data from and/or transmit data to the other unit or component. This can refer to a direct or indirect connection that can be wired and/or wireless in nature. Additionally, two units or components can be in communication with each other even though the data transmitted can be modified, processed, routed, and the like between the first and second unit or component. For example, a first unit can be in communication with a second unit even though the first unit passively receives data and does not actively transmit data to the second unit. As another example, a first unit can be in communication with a second unit if an intermediary unit processes data from one unit and, transmits processed data to the second unit. It will be appreciated that numerous other arrangements are possible.

The present invention is generally directed to a system 100, 150 for remote monitoring and control of one or more spas 10 using a computer or handheld electronic device (e.g., smartphone) with Internet connectivity. The system 100 can be configured to permit remote monitoring and control of one or more spas 10 utilizing a web-based portal or App accessible by a spa owner, spa dealer, or another authorized party. The web portal or App provides a user interface (shown in FIGS. 5 and 6) which allows a user to: control different components and devices on the spa 10; schedule spa operations remotely; and review real-time or previously collected data (e.g., diagnostic information, pump/heater data, water parameters, fault logs, etc.) uploaded from the spa 10 to the website. The user interface may also provide notifications about faults or errors identified by the spa controller and scheduled maintenance activities.

Spa Components

Figure 1:
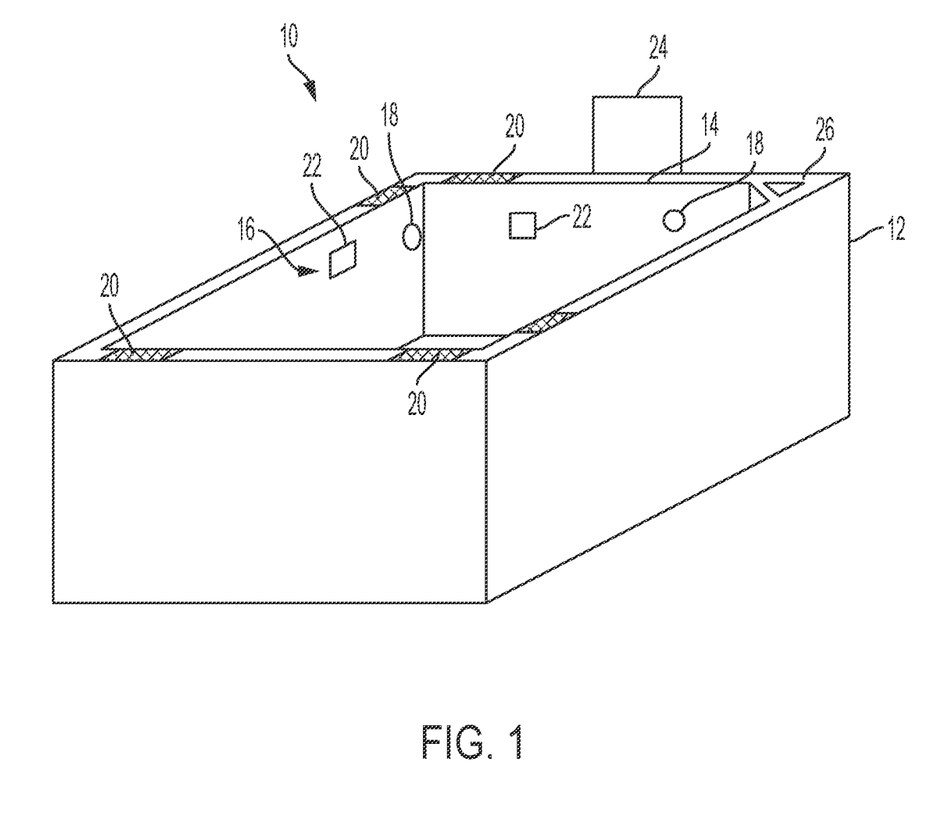
FIG. 1 is a top perspective view of a spa including a communications interface for communicating with a remote control system according to an aspect of the disclosure.

An example of a hot tub or spa 10 is shown in FIG. 1. The spa 10 can include a frame 12, a shell 14, and a basin 16. The frame 12 of the spa 10 is the skeleton of the spa 10 and outlines the basic shape of the spa 10. The shell 14 can cover at least a portion of the frame 12 and can give the spa 10 a more finished appearance. The basin 16 can be defined by the shell 14 of the spa 10 and is a cavity configured to receive and retain water.

In some examples, the spa 10 can also include a number of additional components for improving user experience. For example, the spa 10 can include one or more jets 18 for providing a pressurized stream of water or air into the basin 16. Jets 18 can be arranged at different locations in the basin 16, such as to provide air or water flow to areas of the user's body (e.g., arms, back, legs, neck, etc.), which may benefit from increased pressure. The spa 10 can also include audio/visual entertainment features for providing entertainment or distraction while using the spa 10. Components of the entertainment features, such as speakers 20, lights 22, or a television display 24, may be positioned at different portions of the frame 12 or shell 14.

The spa 10 also includes a main control panel 26 for controlling operation of the spa components. The control panel 26 can include buttons and switches for controlling the spa or can include a touchscreen display. The control panel 26 can also include a visual display for showing which spa components are turned on or off and for displaying information collected by sensors. For example, the display can show a current water temperature and/or a target water temperature.

Figure 2:
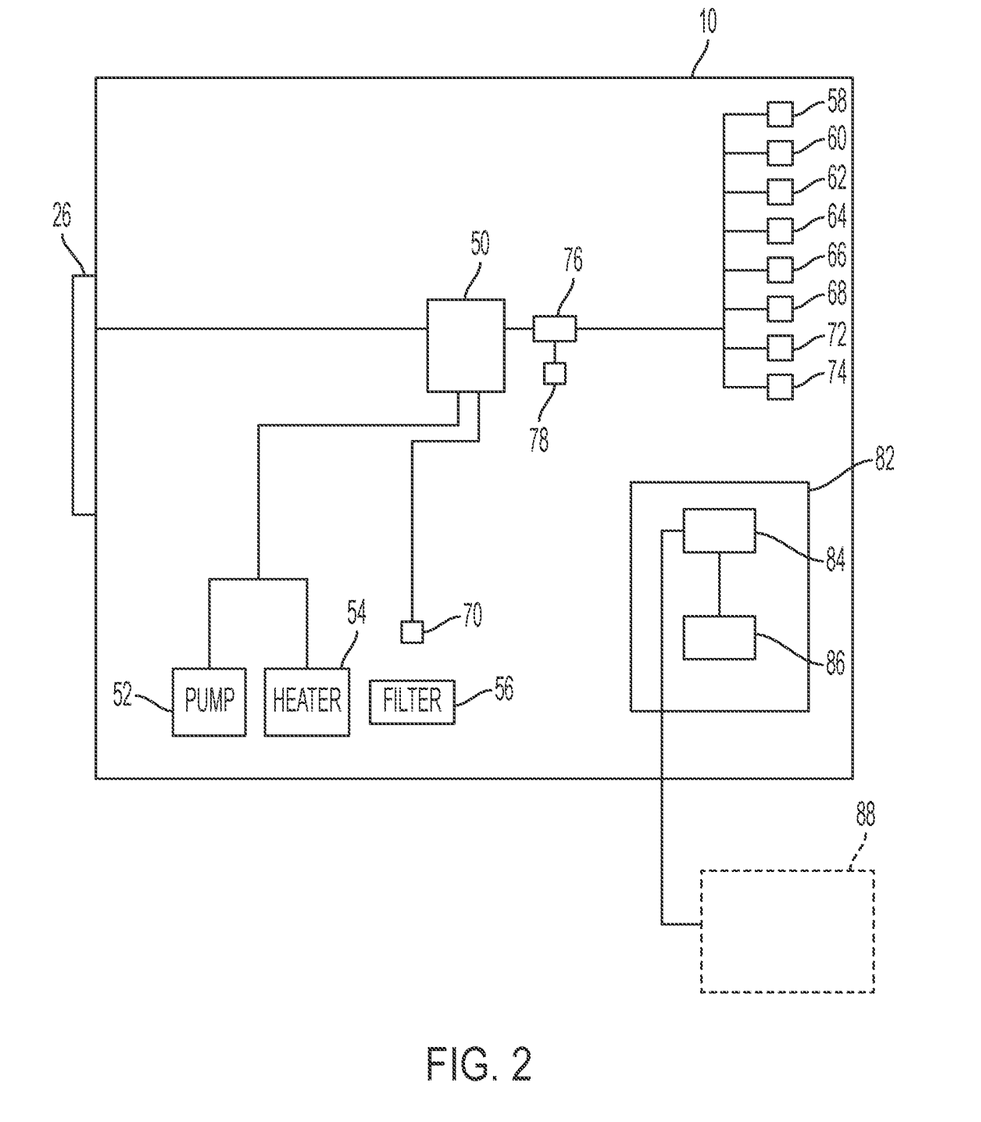
FIG. 2 is a schematic drawing of electronic components of the spa of FIG. 1.

A schematic drawing of electronic components of the spa 10 is shown in FIG. 2. The spa 10 can include a controller 50 in electrical communication with the control panel 26 and with a plurality of onboard sensors. The controller 50 can be a computer processor or computer device, as is known in the art, including computer readable memory with instructions that, when executed, cause the controller 50 to receive information from sources including the on-board sensors, user input devices, the control panel 26, as well as from remote sources through a communication interface, process the received information, and control operation of the spa 10 based on the received information. The controller 50 may also be configured to cause the communications interface to send processed information to remote devices.

As is known in the art, the spa 10 includes electronic devices for conditioning water contained in the basin 16. For example, the spa 10 can include an electric circulation pump 52 and a heater 54. The spa can also include an ozone system or UV system 57 for sanitizing the spa water. The circulation pump 52 can be configured to conduct water from the basin 16 through a filter 56 and the heater 54 back to the basin 16. The pump 52 and heater 54 can be electrically coupled to the controller 50 and configured to receive operating instructions from the controller 50. For example, the controller 50 can be configured to turn the pump 52 and heater 54 on or off based on input from the user or measurements from sensors for measuring water parameters (e.g., temperature, pH, turbidity, etc.) contained in the basin 16. In one example, a target water temperature value can be preset or entered by the user. The controller 50 can be configured to activate the pump 52 and heater 54 when a measured water temperature is below the target value and to turn off the pump 52 and heater 54 when the water temperature is at or above the target value.

As indicated above, the spa 10 also includes a plurality of different types of onboard sensors for monitoring a condition of the spa water and spa components. Sensors for measuring a condition of the water can include a water temperature sensor 58 disposed in the basin 16 or tubing between the basin 16 and pump 52. The spa 10 can also include sensors for measuring water chemistry. For example, a water care or chemical sensor 60 may measure water pH or sanitizer levels (e.g., chlorine level) to ensure that spa chemicals are being provided in an expected manner. In some examples, the spa 10 can include a turbidity sensor 62 positioned in the basin 16. The turbidity sensor 62 can be configured to measure whether water in the spa 10 is clear or cloudy. The spa 10 can also include environmental sensors, such as an ambient temperature sensor 64 and an ambient humidity sensor 66.

In some examples, the spa 10 can also include or be configured to use information acquired from an optical sensor 68 configured to read or record results from different analyte test strips. For example, the optical sensor 68 can be a camera which records an image of a test strip before and after water has been exposed to the strip. The captured images can be processed by the spa controller 50 to determine test results.

The spa 10 also includes sensors for measuring a condition of spa components. For example, the spa 10 can include a flow sensor 70 positioned near the filter 56 for measuring water flow through the filter 56. A decrease in water flow through the filter 56 would indicate that the filter 56 is clogged or full and should be cleaned or replaced. The spa 10 can also include power sensors 72 for measuring incoming power and current drawn by certain spa electronics. The power sensor 72 would identify a loss of electrical power to the spa 10 from, for example, a loss of electricity. The power sensor 72 can also identify power drawn by different spa electronics. Large changes in power used by an electronic component would indicate that the component is operating in an unexpected manner and may need to be serviced or replaced.

In other examples, the power sensor 72 is configured to measure electrical current or power provided to the spa 10 from a power source, such as an electrical outlet. For example, the power sensor 72 could be connected to and/or in electrical communication with a main power line extending from a plug configured to be connected to an electrical outlet. In that case, the power sensor 72 measures power (e.g., phase and magnitude of AC current) provided from the power source to the spa 10. For example, measurements from the power sensor 72 could be used to determine when voltage applied to the spa 10 is too low (e.g., 120 volts instead of 240 volts). Measurements from the power sensor 72 could also be used to identify loss of power or power surges. Information about power loss or surges could be provided to the user through the communications features described herein.

In some examples, the spa 10 can also include sensors for monitoring a condition of the spa 10 during shipping and prior to installation. For example, the spa 10 can include inertia or motion sensors, such as one or more gyroscopes or accelerometers 74, for identifying if the spa 10 has been mishandled (e.g., dropped or damaged in another manner) during shipping. For example, the gyroscopes or accelerometers 74 can be configured to identify linear movement or acceleration of the spa 10, which would indicate that the spa 10 was dropped or fell over, as may occur if the spa 10 is not properly secured during shipping. Information received from the gyroscopes or accelerometers 74 can also be used to identify sudden impacts or severe vibration of the spa 10, as would occur if the spa 10 were hit or otherwise contacted by objects with sufficient force to damage the spa shell 14 or electronic components contacted therein. In other examples, pressure sensors, strain gauges, and similar sensing devices can be used in combination with the gyroscopes and accelerometers 74 to identify drops or impact. For example, pressure sensors could be positioned on different portions of the spa shell 14 and configured to measure impact force against the portions of the shell 14.

In order to operate the sensors during shipping and prior to installation, the spa 10 further includes a battery 76 for providing power to the controller 50 and sensors when the spa 10 is not connected to a power source. In that case, the spa 10 can also include a battery level sensor 78 for measuring a battery level of the battery 76. The spa 10 may also include a location determining sensor or location determining circuitry, such as a global positioning system (GPS) device 80, for monitoring a location of the spa 10 during shipping.

The spa 10 also includes a communications interface 82, such as a cellular or wireless transceiver, for communicating information from spa 10 to a central server or monitoring station and for receiving operating instructions from the central server or monitoring station. In a preferred example, the communications interface 82 is a cellular transceiver 84. In that case, the interface 82 can also include a transceiver battery 86 for powering the transceiver 84 if electric power is lost. The battery 86 can also be configured to provide power to the transceiver 84 during shipping, when the spa 10 is not connected to an electrical outlet, for providing information about the shipping process (e.g., tracking and drop detection features). In some examples, the spa 10 is configured to upload data to and receives instructions from a remote computer network through the cellular transceiver 84. In most cases (e.g., when the spa 10 is located in an area with high-bandwidth cellular reception), the spa 10 communicates through the cellular transceiver 84 and cellular network. In particular, once the spa 10 is installed at an installation location, the cellular transceiver 84 is configured to establish a steady periodic contact with an area cellular network for providing a steady connection therewith.

If cellular reception is not available, a WiFi dongle or adapter 88 can be used to communicate with a user's home wireless network. In that case, data is sent from the spa 10 to the WiFi adapter 88 by a cellular signal sent by the cellular transceiver 84. The WiFi adapter 88 converts the cellular signal to a WiFi signal. The WiFi signal is transmitted to the remote server or to the Internet using a home wireless network and internet connection.

In some examples, the spa 10 is configured to receive wireless software updates through the communications interface 82. In some cases, a software update can be sent in response to a detected fault. In other examples, a spa manufacturer may send software updates to multiple spas at different locations at the same time. In some cases, users may need to agree or opt-in to receive automated software updates.

Spa Control System

Figure 3:
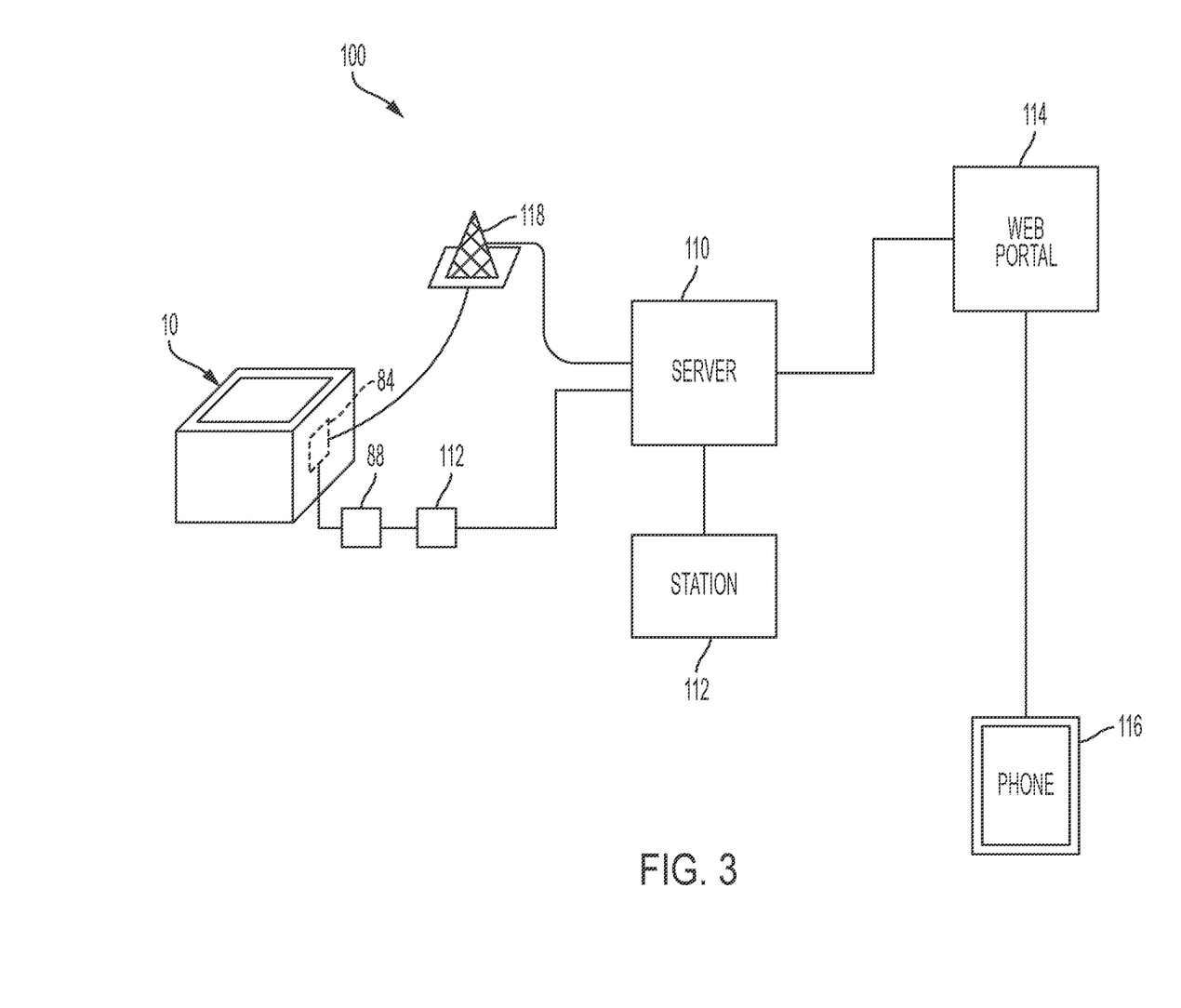
FIG. 3 is a schematic drawing of a remote control system for communicating with the spa of FIG. 1.

A system 100 for remotely monitoring and controlling the spa 10 is shown in FIG. 3. As described above, the spa 10 is configured to send information to and receive instructions from a central server 110. Communication between the spa 10 and central server 110 is preferably over a cellular network through the cellular transceiver 84 located on the spa 10 and one or more cellular towers 118 of the network. Communication with the central server 110 can also be over the Internet through the WiFi dongle or adapter 88 and a user's WiFi router 112 (shown in FIG. 3) and home network.

The central server 110 can be a cloud-based computer network and database including a communications or network interface and memory for storing computer readable information about the spa 10. For example, sensor readings obtained by the spa 10 can be stored on the cloud based network. In addition, user preferences, error logs, maintenance schedules, and similar information for operating the spa 10 can also be stored on the server 110. In some examples, the central server 110 is maintained by a spa manufacturer and includes information about the spa, such as baseline diagnostic test values, obtained before the spa 10 was shipped. In that case, as described herein, certain diagnostic activities can be performed remotely on the central server 110.

The central server 110 can be associated with a manned monitoring station 120, such as a customer service facility manned by service technicians. In that case, information collected by the spa 10 and sent to the central server 110 can be manually reviewed. If certain faults are detected, service technicians can schedule a service call or other appropriate action.

The central server 110 can be associated with a user accessible website or web portal 114 including a user interface for displaying information collected by the sensors associated with the spa. As is known in the art, a web portal is a website or Internet location that displays information from different sources such as other internet-enabled devices, databases, other webpages, and other networks. The website or web portal 114 can also be used for remotely controlling the spa in real time or for scheduling spa operations for a future time. The web portal 114 can be accessed by a spa user with a portable electronic device, such as a smartphone 116. Exemplary user interface screens, which can be displayed on the web portal, are shown in FIGS. 5 and 6.

Figure 4:
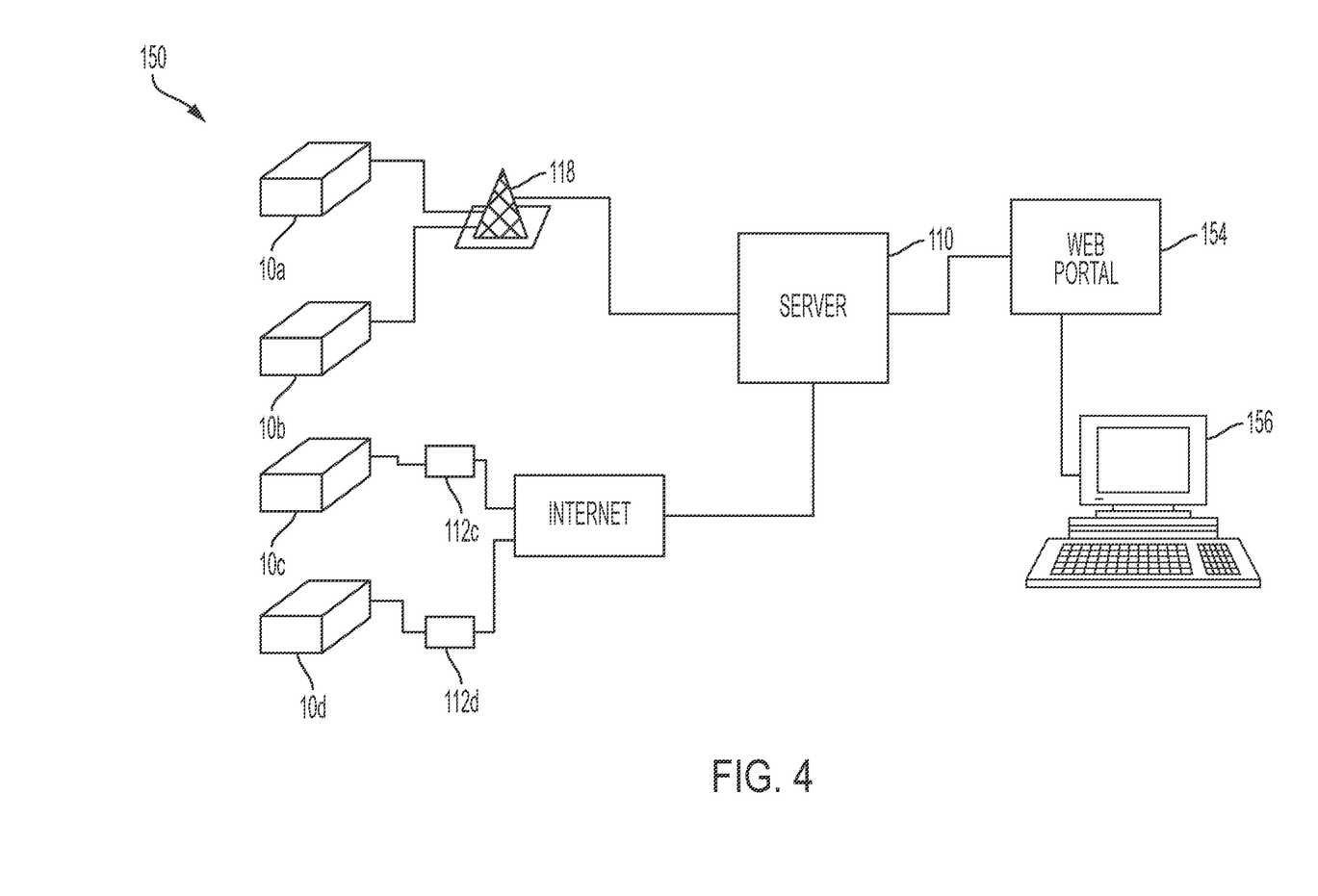
FIG. 4 is a schematic drawing of a system for remote control and monitoring of a fleet of spas.

As shown in FIG. 4, a system 150 for remotely receiving information from and controlling multiple spas 10*a*, 10*b*, 10*c*, 10*d* is illustrated. The system 150 can be used by a spa dealer to monitor a fleet of spas and to provide service if faults or errors are identified. The system 150 includes the central server 110 in wired or wireless communication with the spas 10*a*, 10*b*, 10*c*, 10*d*. As previously described, some spas 10*a*, 10*b* communicate with the central server 110 over a cellular network including cell towers 118. Other spas 10*e*, 10*d* communicate with the central server 110 over the WiFi routers 112*c*, 112*d* and the Internet 154. The central server 110 is configured to receive information from the spas 10*a*, 10*b*, 10*e*, 10*d*, process the information, and make the information available to the spa dealer or another third party over a dealer web portal 154. The spa dealer can access the web portal 154 using a computer 156 or similar device for reviewing the status of the multiple spas 10*a*, 10*b*, 10*c*, 10*d*. In some examples, the dealer can also remotely control the spas 10*a*, 10*b*, 10*c*, 10*d* by entering instructions through a user interface on the web portal 154.

User Interface

Figure 5:
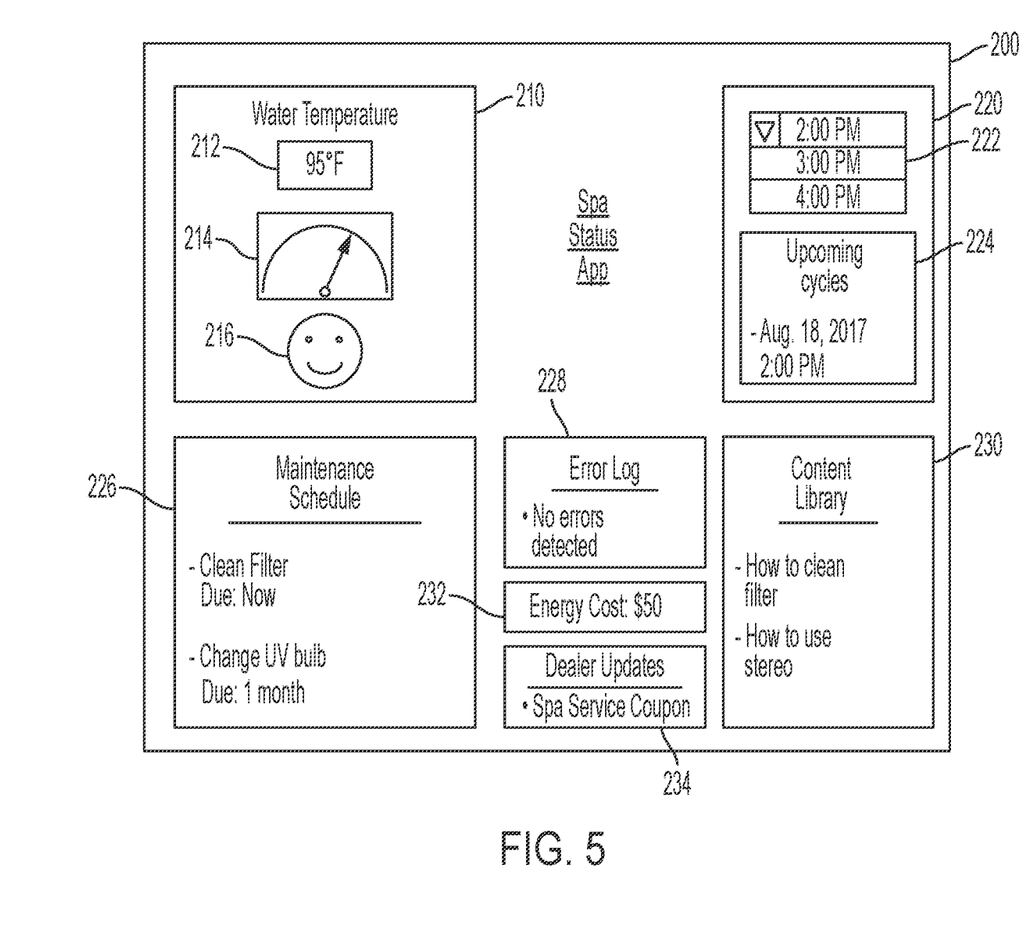
FIG. 5 is an illustration of a user interface screen for remotely monitoring and controlling a spa according to an aspect of the disclosure.
Figure 6:
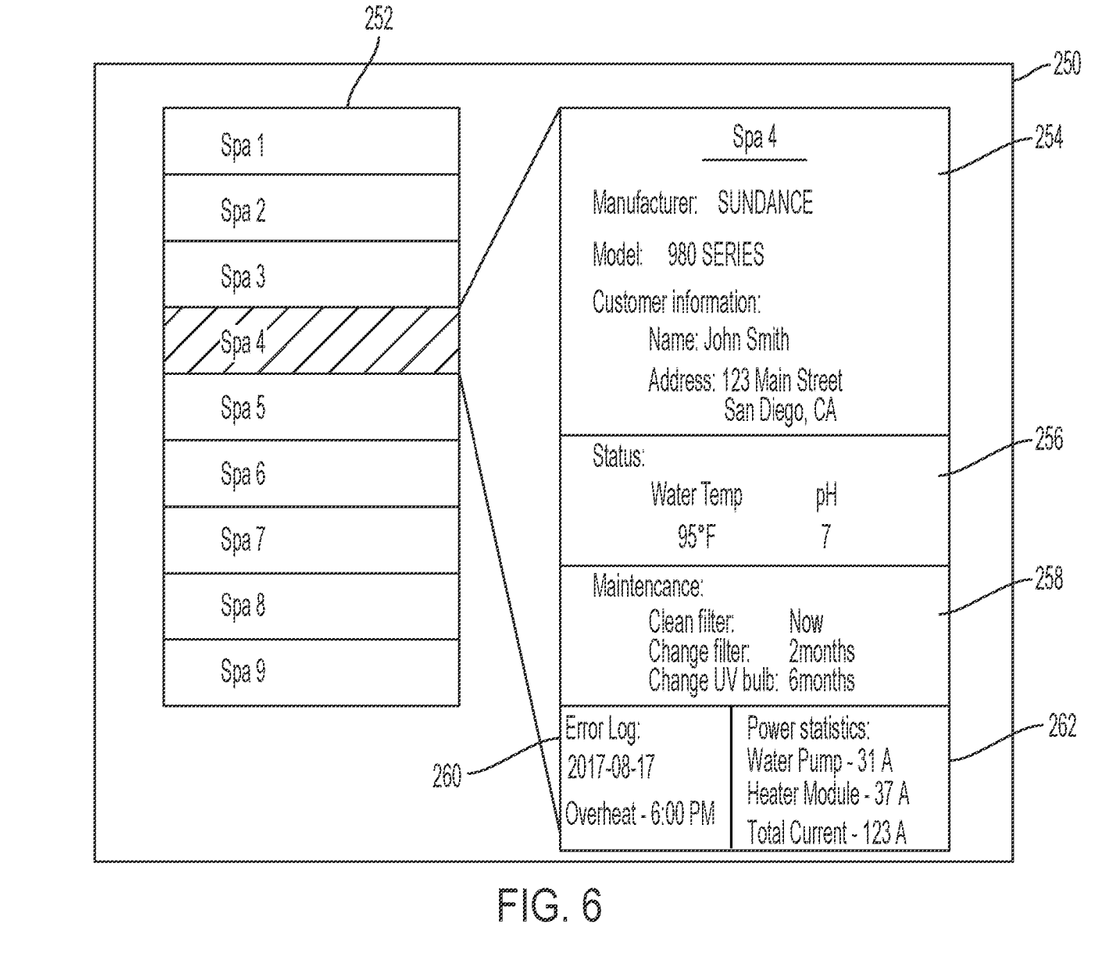
FIG. 6 is an illustration of a user interface for a spa dealer for remote monitoring of a fleet of spas according to an aspect of the disclosure.

An exemplary user interface screen 200 for the website or web portal accessible by a user for monitoring and remotely controlling the spa is shown in FIG. 5. The exemplary screen 200 includes a plurality of sections with different information about the spa 10 and related topics. In some examples, the user interface screen 200 can be customizable. For example, the user may be able to adjust the position of certain screen sections. In addition, the user may be able to close or minimize certain screen sections if the information contained therein is not of particular interest.

In some examples, the user interface screen 200 includes a dashboard section 210 for remotely monitoring the status of the spa 10. On the dashboard section 210, a user can remotely view information collected by sensors associated with the spa 10. The dashboard section 210 can be a visual dashboard including numerical values 212 for sensor readings, along with graphical representations. For example, a visual representation 214 of gas gauges or similar icons can be used for providing information about a spa. As shown in FIG. 5, the dashboard section 210 includes a water temperature indicator displaying current spa water temperature. The dashboard could also display past temperature values. Similar visual representations for power consumption and other operating parameters can also be displayed on the dashboard section 210.

In some examples, the dashboard section 210 of the user interface screen 200 also includes a water quality indicator 216 based on measurements obtained from the water quality and water care sensors on the spa 10. The water quality indicator 216 can be a numerical value, such as an analyte concentration value, water pH, or sanitizer levels. In other examples, a visual icon representative of whether the spa water is clear or cloudy can be displayed. Advantageously, these features allow the user to know, while away from home, whether water is sufficiently clear and that the spa is ready for use. In some examples, the user interface screen 200 can also provide dosing recommendations, which can include displaying exact steps to adjust the spa water using standard spa chemicals.

In some examples, the dashboard section 210 of the user interface screen 200 can also report information collected from a test strip exposed to spa water. For example, the user interface screen 200 can guide a user through exposing a water chemical test strip to water and capturing an image of the test strip using an optical sensor associated with the spa or a separate digital camera device. In either case, the spa controller or a controller associated with the central server can process the captured image to extract color-change information from the test strip. The controller can determine water quality information based on the extracted color change information. The water quality information can be displayed on the dashboard section 210 of the user interface screen 200.

In some examples, the user interface screen 200 can also include a section 220 for remotely programming filtration settings or a pump operation schedule for the spa. For example, the section 220 can include a menu 222 for selecting a filtration cycle time. The section 220 may also include a list 224 of upcoming scheduled filtration cycles. If a filtration cycle is being performed, the section 220 can show status information, such as time remaining in the filtration cycle, to show the user when the spa 10 will be ready for use.

In some examples, the user interface screen 200 can also include a maintenance alert or reminder section 226 including a list of maintenance activities that should be performed now or in the near future. Reminders that can be provided to a user can include a reminder to clean the filter, replace the filter, or change water. Maintenance alerts can be scheduled automatically based on time or date. For example, a clean filter alert may be generated on a regular basis, such as every 3 to 4 months. A reminder to replace a filter can be provided every 8 to 12 months. A reminder to replace a UV sanitizing bulb of the UV system 57 can be provided annually. In other examples, maintenance alerts may be generated based on information collected by spa sensors. For example, a maintenance alert to clean the filter or check the UV bulb may generate if a water quality sensor measures an unexpected value.

The user interface screen 200 can also include an error alert section 228 listing faults detected for spa components. Errors are typically related to a spa component (e.g., the pump or heater) that is not functioning in an expected manner. Sometimes, the spa is configured to generate multiple error alerts, which could be related to one component or to several components. For example, the system may be configured to monitor current or voltage for different components, such as the pump or heater. An alert may be generated if current drawn or power usage by the spa components is outside of a normal operating range. In some examples, faults may be identified by the spa controller based on measurements from spa sensors. In other examples, as described in greater detail hereinafter, faults may be detected by the central server based on a comparison of baseline values for the spa obtained before the spa is shipped to the dealer or customer and operating values measured by spa sensors.

The error alert section 228 of the user interface screen 200 can include a list of detected errors identified by the spa controller or cloud-based central server. The error alert section 228 can also include visual indicators representative of an importance of a particular alert. For example, alerts that are particularly important and require user action may be shown in red or bold text. Less important alerts, which can be addressed at a later time, can be shown in yellow or green text. In addition to viewing errors on the web portal, a user may also be notified of a generated alert on the spa itself. For example, the control panel 26 (shown in FIGS. 1 and 2) may emit a visual or audible notification informing the user that an alert has been generated. In a similar manner, the control panel 26 may also provide a visual or audio notification if a maintenance activity needs to be performed.

Error alerts or notifications about maintenance activities to be performed can also be sent directly to a user by text message or email. Alerts may also be sent to the spa dealer, so that the spa dealer can reach out to the customer to proactively schedule a service appointment if needed or help with basic troubleshooting over the phone.

The user interface screen 200 can also include a user information or content section 230 allowing users to view information, such as articles, how-to guides, and instructional videos, about operating and maintaining the spa. The content section 230 can include a list of available instructional videos that a user can watch to learn about the spa. The content section 230 can also include search features or an index allowing a user to find content of particular interest. The content section 230 can also include a notification about selected recommended content for the user to watch. As described herein, content recommendations can be based on how long the user has owned the spa or use information for the spa collected by onboard sensors.

In some examples, instructional videos can include use and care tips for activities including filling the spa or changing the water, selecting and applying spa chemicals, replacing a UV sanitizing bulb, cleaning or changing the spa filter, programing water filtration, and cleaning the spa. The videos can also include instructions for controlling different spa functions. For example, videos can explain how to operate the spa pump, jets, or entertainment features such as a stereo.

In some examples, a user can access a video by clicking on a video of interest or by keyword searching. For example, a search for the word "filter" may return videos with instructions for removing the filter, cleaning the filter, purchasing a new filter, and installing the new filter. When a video or other content is selected, it can be displayed on a pop-up window or Internet browser screen on the user's computer, smartphone, or other portable electronic device.

In some examples, the system is configured to select relevant videos for users to watch. For example, certain videos may be scheduled to be displayed at a predetermined period of time after initial set up of the spa. In that case, a video about how to operate the pump and jets may be shown to the user a day or two after initial installation. A video instructing the user about how to perform more complex tasks, such as operating a spa stereo or lights, may be displayed a week after installation. A video about changing the filter may be displayed along with the change filter maintenance notification 3, 6, or 12 months after initial installation.

In other examples, sensor information or other inputs received by components on the spa may be used to determine suggested videos for the user to watch. For example, if the user attempts to set a temperature outside of a normal range using the spa control box or if the user presses buttons on the spa control box in an unexpected manner, a video with instructions for operating the circulation pump or explaining the purpose of different buttons on the spa control box may be displayed to the user. In a similar manner, if use records recorded by the spa indicate that the user often uses some entertainment features (e.g., the stereo), but not others (e.g., lights), the system may determine that the user does not know how to use the other components. In that case, an instructional video can be recommended and shown with instructions for using the component. For example, the video may instruct the user how to turn on spa lights, how lights can be used in combination with audio (e.g., visual effects), and other features.

In some examples, the user interface screen 200 also includes an energy cost estimator 232. The energy cost estimator 232 displays an estimated energy cost for operating the spa over a period of time. In some instances, the energy cost estimator 232 displays an estimated number of kilowatt hours (kwh) used by the spa over a period of time (e.g., kwh used in the past week or month). A user can use the displayed number of kwh to determine energy cost. In other examples, the system allows the user to input a local energy rate (e.g., cost per kwh). Based on the input rate information, the energy cost estimator 232 displays an estimated operating cost range. For example, an estimated range for monthly energy costs can be provided. This feature allows the user to track the operation cost through the month. If operating costs are high, the user can adjust spa operating settings to lower costs. However, since the energy cost estimator 232 is not based on actual power consumption of the spa, it is not an exact cost, but only an estimated range.

In some examples, the user interface screen 200 can also include a section 234 with updates from the spa dealer. For example, the update section 234 can include messages about new products related to the spa owned by the user. The update section 234 can also include coupons and discounts.

Dealer User Interface

As previously described, a system 150 (shown in FIG. 4) allows a single user, such as a spa dealer, to monitor and control multiple spas at the same time provided that the user has authorization to access each spa. In that case, the spa dealer can have a dedicated web portal showing status and operating parameters for each spa. The spa dealer can access the website to view information about each spa and to respond to any detected faults. In some examples, the dealer can also control spa components remotely. For example, the dealer can remotely perform troubleshooting activities, such as turning the circulation pump on or off to see if it is working correctly.

A user interface 250 for the web portal, which can be shown to a spa dealer showing status information for multiple spas, is shown in FIG. 6. The user interface 250 generally includes a list 252 of different authorized spas, which the spa dealer is authorized to access. The dealer can select a particular spa to view information, shown at section 254, about the selected spa including, for example, the spa type (e.g., manufacturer and model number), owner's name and address, purchase date, and other identifying information. In some examples, the dealer can also view a status dashboard 256 with information about water quality and operating parameters for various spa components to determine whether spa components are functioning in an expected manner. The dealer user interface screen 250 can also include a section 258 with maintenance reminders for a selected spa. If a particular maintenance reminder is due shortly, the dealer can contact the customer to offer guidance on performing proper maintenance and to proactively schedule a service appointment. In some examples, the dealer user interface screen 250 can also include an error log section 260 for a selected spa including a list of errors generated by the spa controller of the selected spa. The error log section 260 can indicate a time and date that a particular error occurred. For example, as shown in FIG. 6, the error log section 260 indicates that an "overheat" error occurred at 6:00 PM on Aug. 18, 2017. In some instances, the dealer user interface screen 250 also includes diagnostic values, such as values for current drawn by various spa components, as shown in the power statistics section 262 of the dealer user interface screen 250. As shown in FIG. 6, the power statistics section 262 includes measured values for spa components, such as the water pump (31 amps) and the heater module (37 amps). The power statistics section 262 also includes a total current measurement, which is a total electrical current drawn by the spa system at a given time.

System Processes

The spa remote control and monitoring system of the present invention can be used for performing a variety of different spa monitoring and control processes.

Figure 7:
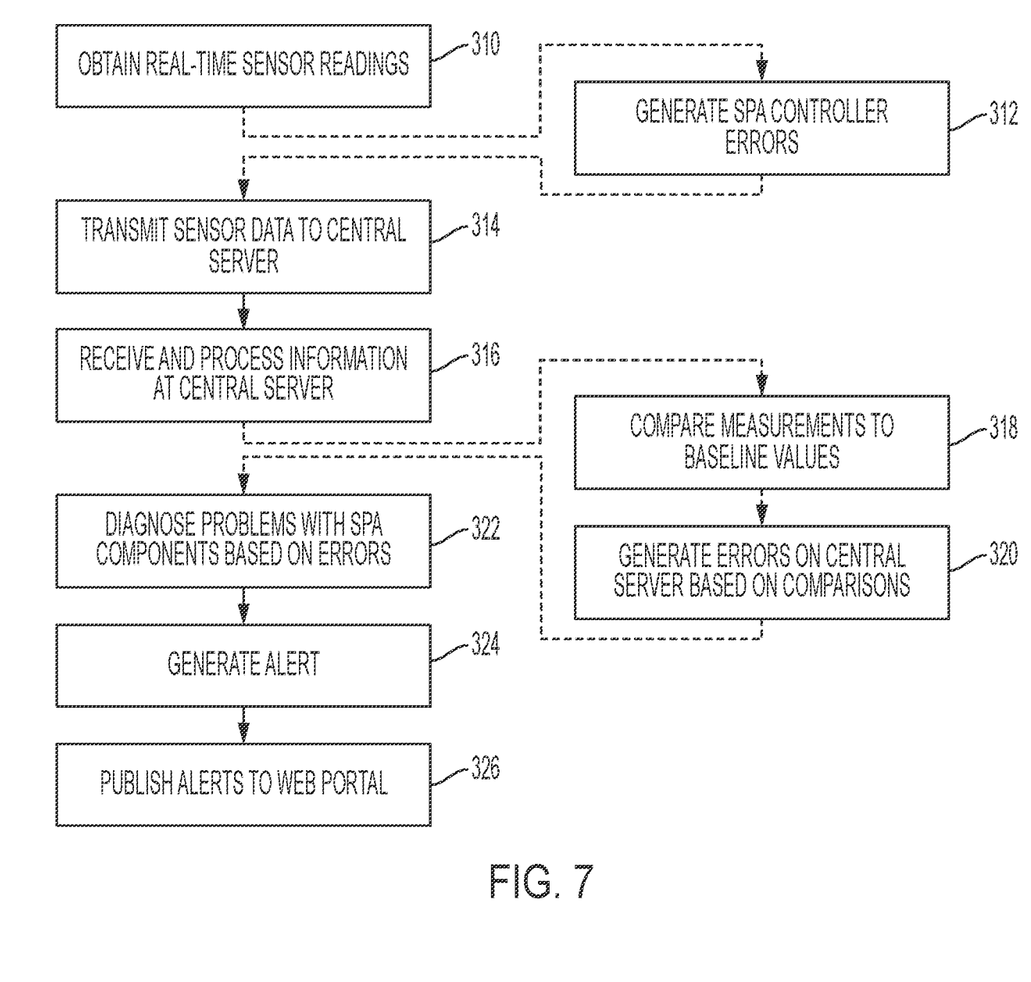
FIG. 7 is a flow chart showing a process for remote diagnostics for a spa according to an aspect of the disclosure.

For example, the system can perform remote diagnostics and generate errors for the spa over a cellular network or the Internet. A flow chart illustrating steps in a process for performing remote diagnostics is illustrated in FIG. 7. In step 310, real-time measurements for sensors associated with spa components are obtained from onboard sensors on the spa. In some examples, the measurements are obtained during normal operation of the spa. In other examples, sensor measurements can be obtained during periodically scheduled or manually initiated self-tests performed by different spa components. A self-test can include cycling power to electronic components of the spa and measuring a response of the respective components. For example, as power is being cycled to the different components, power output for the respective components can be monitored by power sensors (e.g., voltage or current sensors) in electrical communication with different spa components to evaluate whether components are drawing power in an expected manner.

Optionally, as shown at step 312, the spa controller can detect faults to generate errors based on diagnostic measurements obtained by the sensors on the spa. For example, the spa controller can be configured to generate an overheating error when data measured by sensors associated with the pump and/or spa shell indicate that the water is above a predetermined temperature.

At step 314 the data measured by sensors on the spa, such as current or voltage information for electrical components of the spa, is transmitted to the central server over a cellular network or over the Internet, as described herein. Along with the raw data measured by the sensors, information about errors generated by the spa controller can also be transmitted from the spa to the central server. At step 316, received information from the spa is processed by the central server. For example, information about generated errors can be considered and, in some instances, displayed to a user or service technician. Information about generated errors can also be processed to determine, for example, what diagnostic values measured by sensor components may be of particular interest and/or how received measured raw data should be processed and used. The raw data is also received by the central server and processed.

Optionally, at step 318, processed data, such as processed current or voltage information, can be compared to power parameters for the spa stored on the central server. For example, power parameters can include individualized baseline data for a spa, such as baseline current and voltage requirements for each component, startup or wakeup times, times to perform certain functions, and similar parameters obtained for each spa before the spa leaves the manufacturer's warehouse. Based on the comparisons, as shown at step 320, additional errors can be generated by the central server if the measured values fall outside of an expected or acceptable range relative to a baseline valve or exceed a threshold value. In some cases, multiple faults can be identified for a single spa component. In other examples, simultaneous faults for different spa components or a series of faults for different spa components are identified.

As shown at step 322, the central server can be configured to process the errors generated by the spa controller and errors generated by comparison of data on the central server to diagnose problems with spa components. It is recognized that the ability to determine which components generate errors and/or the sequence in which errors are generated by different spa components will help better diagnose and resolve issues. If, based on processing of different generated errors, the central server determines that there is a problem with one or more spa components, an alert may be generated at step 324 indicating that one or more spa components are not functioning in the expected manner. As shown at step 326, the generated error alert can be made available to a user on the web portal, website, or App as previously described. An alert or notification may also be sent directly to a user's portable electronic device (e.g., smartphone) from the central server.

Drain and Fill Assist Process

In another example, the remote control system can be used to provide guidance and feedback while draining or filling the spa. Draining and filling a spa are both time-consuming processes (e.g., draining can take up to an hour) which typically require a user to remain in close proximity to the spa to monitor water levels. The remote control system can be used to provide real-time or periodic updates about a water level of the spa and inform the user when the spa is nearly empty or full.

For example, water level or fill sensors disposed in the basin of the spa can be used to determine a spa water level. Information measured by the sensors can be transmitted from the spa to the central server and, optionally, from the central server to a user's portable handheld electronic device. The received information can also be published to the spa's dedicated web portal or website, where it can be viewed by the user. In some examples, the user interface can include actual water levels, such as a water volume currently contained in the spa basin. Alternatively or in addition, the user interface can display notifications when the spa is nearly full or empty letting the user know when the filling or draining process is completed.

In one example process for changing spa water, a user can prepare to drain the spa in a conventional manner, such as by attaching a hose to a spa outflow port and opening a valve to begin draining water from the spa. The user can then access the spa web portal with a handheld electronic device, such as a smartphone, to view periodic or real-time updates about the spa water level. The user can then walk away from the spa. After a period of time, the user receives an alert on the handheld electronic device indicating that the spa is nearly empty. The user can return to the spa and turn on a water source to begin filling the spa. When the spa is nearly full, the user receives an alert on the handheld electronic device indicating that it is time to return to the spa and turn off the water. Advantageously, due to the remote monitoring capabilities of the system, the user does not need to remain near the spa for the entire duration of emptying and filling.

Tracking Spa Prior to Installation

In some examples, the spa system can be configured to monitor spa location and status prior to installation. For example, readings from sensors associated with the spa can be collected and monitored as the spa is being transported from a manufacturer to a dealer's warehouse or from the warehouse to an installation location. Information measured by sensors on the spa can be wirelessly transmitted to the central server by the cellular transceiver over a cellular network. Since the spa is not connected to a power source during shipping, the sensors and cellular transceiver are powered by the spa battery, as described above.

Measurements from a number of different types of sensors can be useful to monitoring the spa during shipping. For example, accelerometers positioned at different points on the spa frame can be used for drop detection. The accelerometers can be configured to continuously or periodically monitor movement of the spa during shipping. Motion information can be stored locally on computer memory associated with the spa controller. If the accelerometers identify substantial movement indicating that the spa was dropped during shipping, a notification can be sent from the spa to a central server. If a drop is detected, the manufacturer may need to closely examine the spa to ensure that it is suitable for delivery. Alternatively, the manufacturer may need to ship a replacement spa.

The remote control system may also be configured to monitor the spa's location during shipping. For example, the GPS device located on the spa can be configured to periodically wake up and identify a location of the spa. The spa controller can be configured to store the location information on computer readable memory associated with the controller and to periodically or in real-time, send indications of the spa's location to the central server. Information from the GPS device can also be used to monitor the spa's location in the manufacture's production facility or warehouse. Such location information could be used for inventory purposes or to track production time, time spent in the warehouse prior to shipping, and other distribution characteristics that may be of interest to manufacturers and distributors.

The embodiments have been described with reference to various examples. Modifications and alterations will occur to others upon reading and understanding the foregoing examples. Accordingly, the foregoing examples are not to be construed as limiting the disclosure.

The invention claimed is:

1. A monitoring system comprising:
a basin for holding water;
a water circulation system for circulating water contained by the basin;
a sensor for monitoring a water condition or one or more components of the water circulation system;
a communications interface comprising a wireless transceiver;
a controller in electrical communication with the sensor and the communications interface; the controller configured to:
control the one or more components of the water circulation system,
receive information from the sensor,
cause the communications interface to wirelessly transmit the received information to a central server via a first network; and
cause the communications interface to wirelessly transmit the received information to the central server via a second network different than the first network when the first network is not available.

2. The monitoring system of claim 1, wherein the wireless transceiver is a cellular transceiver.

3. The monitoring system of claim 2, wherein the communications interface further comprises a WiFi transmitter.

4. The monitoring system of claim 2, wherein the communications interface further comprises a WiFi adaptor.

5. The monitoring system of claim 1, wherein the first network comprises a cellular network and the second network comprises a WiFi network.

6. The system of claim 1, wherein the sensor comprises a water temperature sensor.

7. The system of claim 1, wherein the sensor comprises a water care sensor for measuring water pH or sanitizer levels of the water.

8. The system of claim 1, wherein the sensor comprises a turbidity sensor.

9. The system of claim 1, wherein the sensor comprises an optical sensor for reading an image of an analyte test strip.

10. The system of claim 1, wherein the sensor comprises an ambient temperature sensor or an ambient humidity sensor.

11. The system of claim 1, wherein the one or more components comprises a filter, and wherein the sensor comprises a flow sensor for measuring water flow through the filter.

12. The system of claim 1, wherein the sensor comprises a power sensor or an electrical current sensor.

13. The system of claim 1, wherein the sensor comprises a location determining circuitry.

14. The system of claim 1, wherein the sensor comprises a water level sensor, and wherein the controller is configured to:
   determine a water level of the basin based on information received from the water level sensor, and
   generate a notification that the basin is nearly full or empty.

15. The system of claim 1, wherein the controller is configured to receive instructions from a remote device or the central server via the communications interface and to adjust an operating parameter based on the received instructions.

16. The system of claim 1, wherein the controller is configured to generate an error or notification based, at least in part, on the information received from the sensor, and wherein the controller is configured to cause the communications interface to wirelessly transmit the error or notification over a cellular network to a remote device or the central server.

17. A system for performing remote diagnostics for a water basin and a water circulation system, the system comprising:
   a sensor for monitoring a water condition or one or more components associated with the water circulation system;
   a communications interface comprising a wireless transceiver configured to transmit information received from the sensor to a central server;
   the central server comprising a computer readable memory storing a baseline measurement, the central server configured to:
      receive sensor information from the communications interface over a cellular network and a WiFi network and receive the sensor information over the WiFi network when the cellular network is not available;
      process the received sensor information to determine a measurement;
      compare the measurement to the baseline measurement stored on the computer readable memory;
      identify a fault based at least in part on the comparison;
      generate an alert based on the fault; and
      transmit the alert to a user computing device.

18. The system of claim 17, wherein the measurement comprises power or current drawn by the one or more components.

19. The system of claim 17, wherein the measurement comprises water flow through a filter.

20. The system of claim 17, wherein the central server is configured to diagnose a problem with the one or more components.

21. The system of claim 17, wherein the central server is configured to transmit a software update to the water basin in response to the identified faults.

22. The system of claim 17, wherein the central server is configured to:
   generate a web portal or app displaying the alert; and
   provide the user computing device with access to the web portal or app.

* * * * *